(12) United States Patent
Kositprapa et al.

(10) Patent No.: US 8,092,831 B2
(45) Date of Patent: Jan. 10, 2012

(54) ANTIHISTAMINE AND DECONGESTANT SYSTEM

(75) Inventors: Unchalee Kositprapa, Davie, FL (US); Mongkol Sriwongjanya, Davie, FL (US)

(73) Assignee: Andrx Pharmaceuticals, LLC, Davie, FL (US)

( * ) Notice: Subject to any disclaimer, the term of this patent is extended or adjusted under 35 U.S.C. 154(b) by 1418 days.

(21) Appl. No.: 10/291,103

(22) Filed: Nov. 8, 2002

(65) Prior Publication Data

US 2004/0091533 A1 May 13, 2004

(51) Int. Cl.
*A61K 9/20* (2006.01)
(52) U.S. Cl. ........ 424/464; 424/465; 424/468; 424/472; 424/474; 424/480; 514/649
(58) Field of Classification Search .................. 424/474, 424/468
See application file for complete search history.

(56) References Cited

U.S. PATENT DOCUMENTS

| | | | |
|---|---|---|---|
| 4,181,719 A | 1/1980 | Margetts et al. |
| 4,282,233 A | 8/1981 | Vilani |
| 4,369,172 A | 1/1983 | Schor et al. |
| 4,552,899 A | 11/1985 | Sunshine et al. |
| 4,576,645 A | 3/1986 | Ravel et al. |
| 4,632,821 A | 12/1986 | Peters et al. |
| 4,650,807 A | 3/1987 | Findlay et al. |
| 4,659,716 A | 4/1987 | Villani et al. |
| 4,692,462 A | 9/1987 | Banerjee |
| 4,695,591 A | 9/1987 | Hanna et al. |
| 4,749,711 A | 6/1988 | Sunshine et al. |
| 4,749,721 A | 6/1988 | Sunshine et al. |
| 4,749,722 A | 6/1988 | Sunshine et al. |
| 4,758,424 A | 7/1988 | Denick, Jr. et al. |
| 4,762,709 A | 8/1988 | Sheumaker |
| 4,777,170 A | 10/1988 | Heinrich |
| 4,792,452 A | 12/1988 | Howard et al. |
| 4,800,087 A | 1/1989 | Mehta |
| 4,801,461 A | 1/1989 | Hamel et al. |
| 4,834,985 A | 5/1989 | Elger et al. |
| 4,839,354 A | 6/1989 | Sunshine et al. |
| 4,915,952 A | 4/1990 | Ayer et al. |
| 4,915,953 A | 4/1990 | Jordan et al. |
| 4,952,402 A | 8/1990 | Sparks et al. |
| 4,959,219 A | 9/1990 | Chow et al. |
| 4,990,535 A | 2/1991 | Cho et al. |
| 4,996,047 A | 2/1991 | Kelleher et al. |
| 4,996,061 A | 2/1991 | Webb et al. |
| 4,999,189 A | 3/1991 | Kogan et al. |
| 4,999,226 A | 3/1991 | Schock et al. |
| 5,004,613 A | 4/1991 | Radebaugh et al. |
| 5,023,076 A | 6/1991 | Ayer et al. |
| 5,024,997 A | 6/1991 | Motola et al. |
| 5,025,019 A | 6/1991 | Sunshine et al. |
| 5,073,380 A | 12/1991 | Babu et al. |
| 5,084,278 A | 1/1992 | Mehta |
| 5,100,675 A | 3/1992 | Cho et al. |
| 5,126,145 A | 6/1992 | Evenstad et al. |
| 5,141,961 A | 8/1992 | Coapman |
| 5,169,638 A | 12/1992 | Dennis et al. |
| 5,215,755 A | 6/1993 | Roche et al. |
| 5,272,137 A | 12/1993 | Blase et al. |
| 5,288,503 A | 2/1994 | Wood et al. |
| 5,296,233 A | 3/1994 | Batista et al. |
| 5,314,697 A * | 5/1994 | Kwan et al. .................. 424/480 |
| 5,385,941 A | 1/1995 | Fawzi et al. |
| 5,405,617 A | 4/1995 | Gowan, Jr. et al. |
| 5,409,907 A | 4/1995 | Blase et al. |
| 5,429,825 A | 7/1995 | Reo et al. |
| 5,431,916 A | 7/1995 | White |
| 5,451,409 A | 9/1995 | Rencher et al. |
| 5,458,879 A | 10/1995 | Singh et al. |
| 5,466,865 A | 11/1995 | Geyer et al. |
| 5,489,436 A | 2/1996 | Hoy et al. |
| 5,510,389 A | 4/1996 | Dhabhar |
| 5,518,730 A | 5/1996 | Fuisz |
| 5,529,783 A | 6/1996 | Burke et al. |
| 5,543,405 A | 8/1996 | Keown et al. |
| 5,560,913 A | 10/1996 | Kupper |
| 5,560,921 A | 10/1996 | Damani et al. |
| 5,595,997 A | 1/1997 | Aberg et al. |
| 5,602,182 A | 2/1997 | Popli et al. |
| 5,616,621 A | 4/1997 | Popli et al. |
| 5,641,512 A | 6/1997 | Cimiluca |
| 5,648,358 A | 7/1997 | Mitra |
| 5,654,005 A | 8/1997 | Chen et al. |
| 5,658,589 A | 8/1997 | Parekh et al. |
| 5,658,919 A | 8/1997 | Ratnaraj et al. |
| 5,660,833 A | 8/1997 | Medenica |
| 5,662,936 A | 9/1997 | de Haan et al. |
| 5,663,415 A | 9/1997 | Chopdekar et al. |
| 5,681,577 A | 10/1997 | Lech et al. |
| 5,691,370 A | 11/1997 | Cupps et al. |
| 5,698,220 A | 12/1997 | Cardinal et al. |
| 5,759,579 A | 6/1998 | Singh et al. |
| 5,763,449 A | 6/1998 | Anaebonam et al. |
| 5,795,574 A | 8/1998 | Breton et al. |
| 5,807,579 A | 9/1998 | Vilkov et al. |
| 5,827,852 A | 10/1998 | Russell et al. |
| 5,834,019 A | 11/1998 | Gregely et al. |
| 5,837,379 A | 11/1998 | Chen et al. |
| 5,840,337 A | 11/1998 | Cody et al. |
| 5,858,409 A | 1/1999 | Karetny et al. |
| 5,859,060 A | 1/1999 | Platt |

(Continued)

OTHER PUBLICATIONS

Steadman's Medical Dictionary, 27th Edition.*
Formulating for Controlled Release with METHOCEL cellulose ether; 1987 The Dow Chemical Company.
Using METHOCEL Cellulose Ethers for Controlled Release of Drugs in Hydrophilic Matrix Systems. Jul. 2000 The Dow Chemical Company.
1998 Physicians' Desk Reference disclosure for Claritin-D 12 52nd Edition, pp. 2615-2618.
1998 Physicians' Desk Reference disclosure for Claritin-D 24 52nd Edition, pp. 2618-2620.

*Primary Examiner* — Robert A Wax
*Assistant Examiner* — Hasan Ahmed
(74) *Attorney, Agent, or Firm* — Florek & Endres, PLLC

(57) ABSTRACT

The present invention relates to an oral pharmaceutical formulation that employs: (1) a compressed core containing a decongestant or pharmaceutically acceptable salt thereof; (2) a delayed release coating on the compressed core and (3) immediate release therapeutic amounts of a decongestant and an antihistamine.

10 Claims, 1 Drawing Sheet

U.S. PATENT DOCUMENTS

| | | |
|---|---|---|
| 5,869,098 A | 2/1999 | Misra et al. |
| 5,869,479 A | 2/1999 | Kreutner et al. |
| 5,876,752 A | 3/1999 | Herbig et al. |
| 5,876,759 A | 3/1999 | Gowan, Jr. |
| 5,881,926 A | 3/1999 | Ross |
| 5,891,476 A | 4/1999 | Reo et al. |
| 5,895,663 A | 4/1999 | Irwin et al. |
| 5,916,590 A | 6/1999 | Cody et al. |
| 5,919,481 A | 7/1999 | Cody et al. |
| 5,922,352 A | 7/1999 | Chen et al. |
| 6,114,346 A * | 9/2000 | Harris et al. .................. 514/290 |
| 6,267,986 B1 * | 7/2001 | Jain et al. ..................... 424/472 |
| 6,827,946 B2 * | 12/2004 | Hirsh ............................ 424/472 |
| 2002/0031552 A1 * | 3/2002 | McTeigue et al. ........... 424/490 |
| 2003/0035839 A1 * | 2/2003 | Hirsh et al. ................... 424/471 |

\* cited by examiner

ANTIHISTAMINE AND DECONGESTANT SYSTEM

FIELD OF THE INVENTION

The present invention relates to the field of oral dosage forms and in particular to oral dosage forms that provided an extended release of a decongestant and an immediate release of an antihistamine.

BACKGROUND OF THE INVENTION

The present invention relates to a twelve to twenty-four hour unit dosage form comprising an antihistamine and a decongestant. The unit dosage form is useful in treating patients with colds, the flu and other upper respiratory diseases.

Antihistamines include piperidinoalkanol derivatives which are disclosed in U.S. Pat. No. 4,996,061 and incorporated herein by reference. Piperidinoalkanol compounds are useful as antihistamines, antiallergy agents and bronchodilators. Loratadine is a specific type of piperidinoalkanol and is disclosed in U.S. Pat. No. 4,282,233 as an antihistamine with little or no sedative effect. Another preferred antihistamine is the active metabolite of loratadine, descarboethoxy loratadine, which is described in U.S. Pat. No. 4,659,716.

Antihistamines are often administered in combination with sympathomimetic or decongestant drugs. Those skilled in the art recognize sympathomimetic drugs such as pseudoephedrine, phenylephedrine and phenylpropanolamine as therapeutic agents effective for the relief of nasal congestion.

Some common combinations of antihistamines and sympathomimetics or decongestants are loratadine and pseudoephedrine as sold commercially under the tradenames CLARITIN®-D 12 HOUR and CLARITIN®-D 24 HOUR.

Once and twice daily controlled release formulations containing a combination of loratadine and pseudoephedrine have been described. These formulations can be undesirable for many reasons including deficiencies in safety, effectiveness and ease of manufacture.

In order to encourage high patient compliance the antihistamine dosage unit should be prepared in a unit dosage form that is taken once or twice daily. These formulations should be stable, economical and easy to manufacture.

It is therefore an objective of the present invention to provide a safe and effective twelve to twenty-four hour antihistamine and decongestant formulation.

SUMMARY OF THE INVENTION

The present invention is an oral dosage formulation that provides release of the active ingredients for twelve to twenty-four hours. The dosage formulation comprises a core containing a decongestant that is coated with a pH dependent polymer and at least one immediate release coating on the core. The coating controls the release of the decongestant from the core. The immediate release coating contains an antihistamine and/or a decongestant. In a preferred embodiment there are two immediate release coatings disposed on the coated core, wherein one immediate release coating contains the decongestant and the other immediate release coating contains the antihistamine.

The core comprises a decongestant or pharmaceutically acceptable salt thereof and optionally a filler. The core can be a compressed matrix type tablet or a pellet coated with a polymeric material that controls the release of the decongestant from the core. In a preferred embodiment an immediate release decongestant coating is applied to the core. The immediate release decongestant coating may be seal coated and a second immediate release coating comprising an antihistamine applied to the seal coat. The antihistamine release coating may be applied directly to the decongestant immediate release coating if a seal coating is not employed. The order in which the two immediate release coatings are applied can be reversed. The final dosage formulation may be optionally coated with a seal coating and/or a polishing agent.

DETAILED DESCRIPTION OF THE INVENTION

Figure 1:
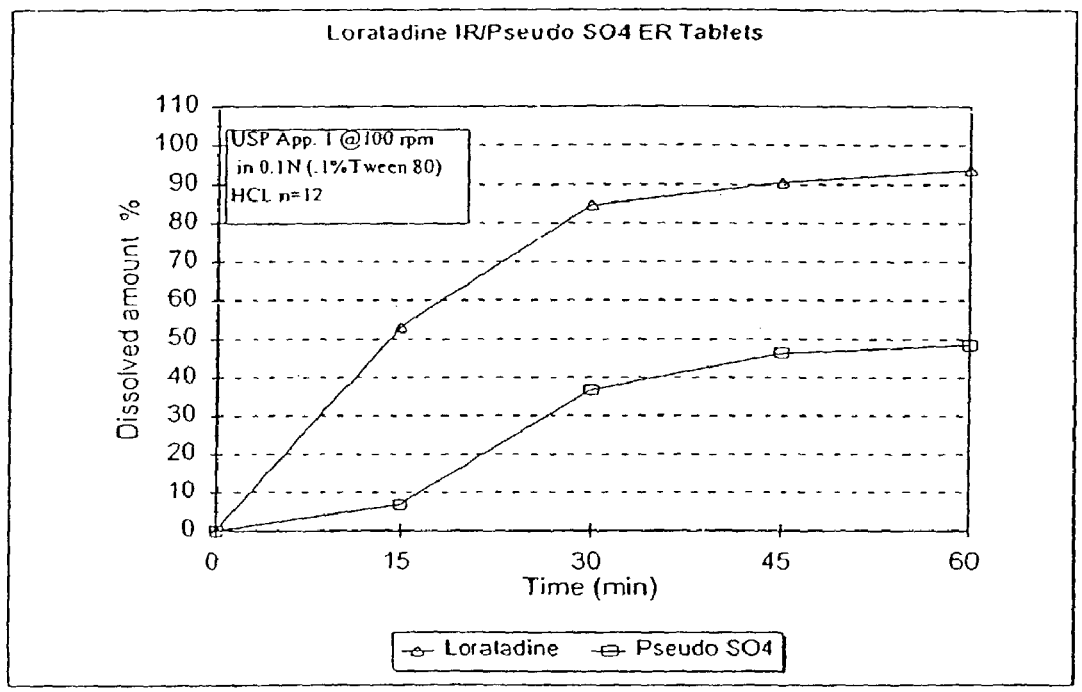
FIG. 1 is a graph that shows the in vitro dissolution rate of an antihistamine and a decongestant from a tablet of the preferred embodiment of the present invention in 0.1 N HCl with 0.1% tween 80.

Stage I Decongestant Immediate Release Tablet or Core

The present invention employs an immediate release core or tablet comprised of a blend of the following materials:

TABLE I

| Materials | Preferred | Most Preferred |
|---|---|---|
| Decongestant | 10-30% | 15-25% |
| Filler | 65-90% | 75-85% |
| Glidant | 0-2% | 0.1-1% |
| Lubricant | 0-2% | 0.1-1% |

The above percentages are based upon the total weight of the tablet or core.

In forming the tablet or core the decongestant and any excipients are mixed together using standard techniques known in the art. The blend is then compressed into tablets using techniques commonly used in the art.

A preferred decongestant is pseudoephedrine. Other possible decongestants include, but are not limited to, phenylephedrine and phenylpropanolamine and other sympathomimetic drugs as well as pharmacologically acceptable salts thereof. A number of other decongestants are identified in Remington's 18th Edition pp. 870-888, and are incorporated herein by reference. The terms "pharmacologically acceptable salts" encompasses both organic and inorganic acid addition salts including, for example those prepared from acids such as, sodium, hydrochloric, hydrofluoric, sulfuric, sulfonic, tartic, fumaric, hydrobromic, glycolic, citric, maleic, sulfate, phosphoric, succinic, acetic, nitric, benzoic, ascorbic, p-toluene sulfonic, benzenesulfonic, naphthalenesulfonic, propionic, and the like.

The filler should be a water soluble or rapidly dispersible inert material. A preferred filler is lactose monohydrate. Other fillers such as starch, dextrose, sucrose, hydroypropyl cellulose, vegetable oils, microcrystalline cellulose and the like may be added.

The preferred glidant is colloidal silicon dioxide. Other glidants commonly used in the art may be used as well.

The preferred lubricant is magnesium stearate. Other examples of suitable tablet lubricants include calcium stearate, stearic acid, hydrogenated vegetable oils, polyethylene glycol, talc, glycerol behenate and glycerol monostearate.

Stage II Decongestant Delayed Release Tablet or Core

Once the decongestant immediate release tablet or core is prepared, it is coated with a delayed release coating comprising the following materials:

TABLE II

| Materials | Preferred | Most Preferred |
|---|---|---|
| pH sensitive polymer | 15-60% | 25-45% |
| Plasticizer | 0-15% | 3-10% |
| Anti-adherent | 30-75% | 40-65% |

The weight percentages are based on the total weight of the delayed release coating.

In a preferred embodiment, the immediate release tablet or core is subsequently coated with a delayed release and/or a pH dependent polymer. This coating is applied by conventional coating techniques, such as pan coating or fluid bed coating using solutions or suspensions of polymers in water or suitable organic solvents. The delayed release coating should be applied so that the pharmaceutical active ingredient present in the core or tablet is released only after the dosage form has passed through the stomach. To insure that the pharmaceutically active ingredient present in the core is not released until the dosage form has left the stomach, the delayed release coating should be designed to dissolve at a pH greater than 4.5, preferably greater than 5.5 and most preferably greater than a pH of 6. The preferred manner in which to obtain a delayed release coating that does not dissolve until the dosage form has passed through the stomach and reached an environment where the pH is higher than 4.5 is to incorporate a pH dependent polymer into the delayed release coating.

Preferably, the pH dependent polymer employed in the delayed release coating is selected from the group consisting of zein, methacrylic acid copolymers, cellulose acetate phthalate, hydroxypropyl methylcellulose phthalate, hydroxypropyl methylcellulose acetate succinate, cellulose acetate trimellitate, polyvinyl acetate phthalate or mixtures thereof. A mixture of zein and methacrylic acid copolymer is most preferred. The methacrylic acid copolymer is selected from the group of pH dependent coating polymers, preferably Eudragit S, and most preferably Eudragit S100. The preferred concentration of zein is 10-40%, most preferably at 15-30% of the total weight of the delayed release coating. The preferred concentration of Eudragit S100 is 0-30%, most preferably at 8-18% of the total weight of the delayed release coating.

The delayed release coating may also preferably comprise plasticizers. Plasticizers which may be used include any of those known to those skilled in the art, including but not limited to acetyltributyl citrate, triacetin, acetylated monoglyceride, rape oil, olive oil, sesame oil, acetyltriethyl citrate, glycerin sorbitol, diethyloxalate, diethylmalate, diethylfumerate, dibutylsuccinate, diethylmalonate, dioctylphthalate, dibutylphthalate, dibutylsebacate, triethyl citrate, tributylcitrate, glyceroltributyrate, polyethylene glycol, propylene glycol and mixtures thereof. The preferred plasticizer is acetyl tributyl citrate in an amount ranging form 0 to about 15%, and most preferably at 3-10% based on the total weight of the delayed release coating.

The delayed release coating may further preferably include an anti-adherent such as those selected from the group consisting of talc, colloidal silicon dioxide, magnesium stearate, magnesium silicate, glycerol monostearates, calcium stearate or steric acid. The preferred anti-adherent is talc in an amount ranging from about 30-75%, and most preferably 40-65% based on the total weight of the delayed release coating.

Stage III Immediate Release Decongestant Layer

In the present invention, the delayed released core or tablets described above (Stage II formulation) are further coated with an immediate release coating comprising the following materials:

TABLE III

| Materials | Preferred | Most Preferred |
|---|---|---|
| Decongestant | 20-70% | 35-60% |
| Binder | 10-50% | 20-35% |
| Plasticizer | 0-15% | 1-10% |
| Anti-adherent | 0-40% | 10-30% |

The above percentages are based upon the total weight of the immediate release decongestant coating. The decongestant employed in the immediate release decongestant layer or coating is a decongestant as previously described. The decongestant employed in the immediate release decongestant layer can be the same decongestant used in the core or a different decongestant.

The binder employed in the immediate release decongestant layer is preferably a pharmaceutically acceptable water-soluble polymer or rapidly dispersing material. The binder can be any type of binding agent commonly known in the art such as sucrose, polyvinyl pyrrolidone, hydroxyethyl cellulose, hydroxypropyl cellulose, Opadry® Clear and low molecular weight hydroxypropyl methylcellulose (HPMC). In a preferred embodiment of the present invention, the binding agent is a water-soluble polymer such as hydroxypropyl cellulose.

A plasticizer may also be added to the immediate release decongestant coating. Polyethylene glycol is the preferred plasticizer. Other plasticizers may be selected from those listed above.

An anti-adherent may also be added to the immediate release decongestant coating. The preferred anti-adherent is talc. Other anti-adherents may be selected from those listed above.

Stage IV Seal Coating

Once the immediate release decongestant coating is applied to the delayed release core, a seal coat may be applied to the immediate release decongestant formulation. If employed, the seal coat should be comprised primarily of a water-soluble polymer or rapidly dispersing material. Some commonly used seal coating materials are sucrose, polyvinyl pyrrolidone, hydroxyethyl cellulose, hydroxypropyl cellulose and hydroxypropyl methylcellulose. In a preferred embodiment the seal coat contains and osmotic agent such as sodium chloride, potassium chloride or lactose that facilitates the rapid disintegration of the seal coat.

Stage V Antihistamine Immediate Release Coating

The present invention also employs an antihistamine immediate release coating. As mentioned above, the antihistamine and decongestant may be incorporated into a single immediate release coating provided the antihistamine, decongestant and excipients are compatible. For example the ingredients in tables III and IV can be combined into one coating when the decongestant is pseudoephedrine sulfate, the antihistamine is loratadine and the surfactant is Tween 80. This combined antihistamine/decongestant immediate release coating eliminates the need for the seal coating step described above in Stage IV.

In a preferred embodiment of the present invention the antihistamine is incorporated into the dosage formulation in a separate and distinct immediate release layer or coating. The antihistamine immediate release layer should comprise:

TABLE IV

| Materials | Preferred | Most Preferred |
|---|---|---|
| Antihistamine | 1-25% | 5-15% |
| Binder | 30-70% | 40-60% |
| Surfactant | 10-40% | 15-30% |
| Anti-adherent | 0-25% | 5-15% |

The above percentages are based upon the total weight of the antihistamine immediate release coating.

The antihistamine is preferably loratadine or its active metabolite descarboethoxy loratadine. The antihistamine may also be selected from the antihistamines described above.

Suitable surfactants are sodium lauryl sulfate, sodium taurocholate or a polysorbate. The preferred surfactant is sodium lauryl sulfate.

The anti-adherents and binders are previously described. The preferred lubricant is talc, and the preferred binder is Opadry® Clear YS-1-7006.

Stage VI Second Seal Coating

After the antihistamine immediate release coating is applied, a second seal coating may optionally be applied.

Stage VII Polishing

Finally, a polishing agent may be applied. In a preferred embodiment the polishing agent is comprised of candillia wax and comprises about 0.01-0.1% and preferably about 0.025-0.05% of the total weight of the final dosage formulation.

Antihistamine Release Rates

The formulation prepared in accordance with the present invention will preferably exhibit the following antihistamine release rate in 0.1 N HCl with 0.1% tween 80 using a USP apparatus I at 100 rpm and 37° C.

TABLE V

| Time (minutes) | Amount Dissolved (Preferred) | Amount Dissolved (Most Preferred) |
|---|---|---|
| 15 | 35-75% | 40-60% |
| 30 | 50-90% | 60-90% |
| 45 | 65-95% | 75-95% |
| 60 | NLT 85% | NLT 90% |

NLT = Not Less Than

DETAILED DESCRIPTION OF THE PREFERRED EMBODIMENT

The present invention will be described in detail by reference to the following Example.

Example 1

An oral dosage formulation in accordance with the present invention is prepared by: (I) forming an immediate release pseudoephedrine tablet core; (II) coating the immediate release tablet core with a delayed release coating; (III) applying an immediate release pseudoephedrine coating to the delayed release coating; (IV) seal coating the immediate release pseudoephedrine coated product; (V) applying an immediate release loratadine coating to the seal coated product; (VI) seal coating the immediate release loratadine product; and (VII) applying a polishing coat to the seal coated product. The actual ingredients for each stage and method for manufacturing each intermediate stage is described below.

Stage I Pseudoephedrine Immediate Release Tablets

The core tablet was prepared by blending the following ingredients:

| | |
|---|---|
| 1. Pseudoephedrine | 9.6 kg |
| 2. Lactose monohydrate | 38.02 kg |
| 3. Colliodal silicon dioxide | 0.14 kg |
| 4. Magnesium stearate | 0.24 kg |

The pseudoephedrine, lactose and colloidal silicon dioxide were mixed and then passed through a CoMil with a #1143 screen and a 0.175" spacer at a medium speed and then blended.

The magnesium stearate was separately passed through a #30 mesh screen, added to the above mixture and blended for 5 minutes.

The blend is then compressed into tablets using a tablet press at a hardness of about 8-12 kp, preferably about 10 kp.

Stage II Pseudoephedrine Sulfate Delayed Release Tablets 10.44 kg of the pseudoephedrine sulfate tablets prepared in Stage I above were coated with the following ingredients:

| | |
|---|---|
| 1. Eudragit S100 | 0.196 kg |
| 2. Zein | 0.39 kg |
| 3. Acetyl tributyl citrate | 0.97 kg |
| 4. Talc | 0.88 kg |

Eudragit S100 and zein were added to a solution of isopropyl alcohol and purified water until a clear solution was obtained. Acetyl tributyl citrate was added into the solution while stirring. Talc was also added to the solution while mixing. The resulting coating suspension was stirred throughout the coating process.

The pseudoephedrine sulfate immediate release tablets were added into a tablet coater operated with the following settings.

| | |
|---|---|
| Exhaust temperature | 30° C. |
| Atomization Pressure | 30 psi |
| Air volume | 200 SCFM |
| Pan Speed | 8-15 rpm |
| Spray rate | 30 ml/min |

The coated tablets are dried in the coating pan then transferred from the pan coater to an oven for about 16 hours of further drying.

Stage III Pseudoephedrine Immediate Release Coating

| | |
|---|---|
| 1. Pseudoephedrine Sulfate | 1.386 kg |
| 2. Hydroxypropyl cellulose | 0.804 kg |
| 3. Polyethylene glycol | 0.142 kg |
| 4. Talc | 0.583 kg |

The hydroxypropyl cellulose and polyethylene glycol were added into 16.5 kg of purified water and stirred until a clear solution was obtained. The pseudoephedrine sulfate was added to the solution using a homogenizer and allowed to fully dissolve. The talc was then mixed into the solution using a homogenizer. 0.45 kg of purified water was used to rinse the container holding the polyethylene glycol and the homogenizer. The rinse material was added to the coating solution. A mechanical stirrer was used to stir the coating suspension until it was completely consumed by the coating process.

7.681 kg of the pseudoephedrine sulfate delayed release tablets prepared in Stage II above were added into a tablet coater and coated with the pseudoephedrine immediate release coating suspension prepared above using the following settings.

| Exhaust temperature | 40° C. |
|---|---|
| Atomization Pressure | 2 psi |
| Air volume | 300-320 SCFM |
| Pan Speed | 13 rpm |
| Spray rate | 20 ml/min |

The tablets are dried in the coating pan for about 20-25 minutes.

Stage IV Seal Coating (Seal Coating Solution I)

| 1. Opadry ® Clear YS-1-7006 | 0.219 kg |
|---|---|
| 2. Sodium Chloride | 0.044 kg |

The Opadry® Clear YS-1-7006 and sodium chloride were added into 2.20 kg of purified water and stirred until completely dissolved.

The pseudoephedrine immediate release coated tablets prepared in Stage III above were coated with seal coating solution I using the conditions described in Stage III above. Seal coating solution I was applied to the pseudoephedrine immediate release coated tablets prepare in Stage III immediately after the drying phase and without removing the tablets from the coating apparatus.

Stage V Loratadine Immediate Release Coating

| 1. Opadry ® Clear YS-1-7006 | 0.531 kg |
|---|---|
| 2. Sodium Lauryl Sulfate | 0.231 kg |
| 3. Loratadine | 0.115 kg |
| 4. Talc | 0.115 kg |

The Opadry® Clear YS-1-7006 was added to 8.645 kg of purified water under mechanical stirring. Next, the sodium lauryl sulfate was added to the Opadry® solution and the speed of the mechanical stirrer was reduced to prevent excess foaming. After a clear solution was obtained, the loratadine and talc were mixed into the Opadry® solution with a homogenizer until they were fully dispersed. The homogenizer was removed and rinse with 0.5 kg of purified water. The loratadine suspension was then stirred continuously until completely consumed during the coating process.

The seal coated tablets prepared in Stage IV above were coated with the loratadine coating suspension using the conditions described in Stage III above. The loratadine coating suspension was applied to the seal coated tablets prepare in Stage IV immediately after the drying phase and without removing the tablets from the coating apparatus.

Stage VI Seal Coating (Seal Coating Suspension II)

0.335 kg of Opadry® White YS-1-7003 was added to 3.350 kg of purified water and stirred at high rpm until the big lumps were dispersed. Stirring was continued at low rpm until a homogeneous suspension was obtained and continued throughout the coating process until the solution was fully consumed.

The immediate release loratadine coated tablets prepared in Stage V above were coated with the second seal coating suspension using the conditions described in Stage III above. The second seal coating suspension was applied to the immediate release loratadine coated tablets prepare in Stage V immediately after the drying phase and without removing the tablets from the coating apparatus.

Stage VII Polishing

| 1. Extended Release Tablets | (Batch size 60.81 kg) |
|---|---|
| 2. Candelilla Wax Powder | 0.018 kg |

A polishing coat is then applied to the Stage VI tablets prior to removal from the coating pan. The coating pan, with the inlet heat and exhaust air off, was turned at a speed of 5-6 rpm in order to roll tablets in the pan. The candellila wax was then passed through a #60 mesh screen and sprinkled across the tablet bed. After 5 minutes of rolling, the exhaust fan was turned on and the tablets were rolled for an additional 10 minutes with the inlet heat off.

The dissolution rate of the formulation prepared in this example was tested using a USP, type 1 apparatus at 100 rpm, in 0.1 N HCl with 0.1% tween 80. The results are shown in FIG. 1.

While certain preferred and alternative embodiments of the invention have been set forth for purposes of disclosing the invention, modifications to the disclosed embodiments may occur to those who are skilled in the art. Accordingly, the appended claims are intended to cover all embodiments of the invention and modifications thereof which do not depart from the spirit and scope of the invention.

We claim:
1. An oral pharmaceutical tablet consisting essentially of:
   (a) a delayed release pseudoephedrine sulfate or hydrochloride tablet and
   (b) an immediate release coating applied to said delayed release pseudoephedrine tablet that allows for the immediate release of a therapeutic amount of pseudoephedrine sulfate or hydrochloride and a therapeutic amount of an antihistamine selected from the group consisting of loratadine and descarboethoxy loratadine;
   wherein the delayed release pseudoephedrine tablet consists of:
   (a) a compressed immediate release core consisting essentially of:
      (i) 10-30% based upon the total weight of the compressed core of pseudoephedrine sulfate or hydrochloride;
      (ii) 65-90% based upon the total weight of the compressed core of a filler;
      (iii) 0.1-2% based upon the total weight of the compressed core of a glidant; and
      (iv) 0.1-2% based upon the total weight of the compressed core of a lubricant; and
   (b) a delayed release coating on said compressed immediate release core consisting essentially of:
      (i) 15-60% based upon the total weight of the delayed release coating of a combination of at least two pH dependent polymers selected from the group consisting of zein, methacrylic acid copolymers, cellulose acetate phthalate, hydroxypropyl methylcellulose phthalate, hydroxypropyl methylcellulose acetate succinate, cellulose acetate trimellitate and polyvinyl acetate phthalate;

(ii) 3-15% based upon the total weight of the delayed release coating of a plasticizer; and (iii) 30-75% based upon the total weight of the delayed release coating of an anti-adherent wherein the delayed release coating delays the release of the pseudoephedrine sulfate or hydrochloride from the immediate release core until the delayed release tablet reaches an environment where the pH is higher than 6; and wherein the immediate release coating comprises:

(a) a pseudoephedrine immediate release coating comprising:
(i) a therapeutic amount of pseudoephedrine sulfate or hydrochloride; and
(ii) a water soluble or rapidly dispersible binder; and (b) a separate antihistamine immediate release coating comprising:
(i) a therapeutic amount of loratadine or descarboethoxy loratadine,
(ii) a water soluble or rapidly dispersible binder, and
(iii) a surfactant.

2. The oral pharmaceutical tablet defined in claim 1, further comprising a seal coat between the pseudoephedrine immediate release coating and the antihistamine immediate release coating.

3. The oral pharmaceutical tablet as defined in claim 2 wherein the pseudoephedrine immediate release coating consists essentially of:
(i) 20-70% based upon the total weight of the pseudoephedrine immediate release coating of pseudoephedrine sulfate or hydrochloride;
(ii) 10-50% based upon the total weight of the pseudoephedrine immediate release coating of a binder;
(iii) 1-15% based upon the total weight of the pseudoephedrine immediate release coating of a plasticizer;
(iv) 10-40% based upon the total weight of the pseudoephedrine immediate release coating of an anti-adherent; and the antihistamine immediate release coating consists essentially of:
(i) 1-25% based upon the total weight of the antihistamine immediate release coating of loratadine or descarboethoxy loratadine;
(ii) 30-70% based upon the total weight of the antihistamine immediate release coating of a binder;
(iii) 10-40% based upon the total weight of the antihistamine immediate release coating of a surfactant;
(iv) 5-25% based upon the total weight of the antihistamine immediate release coating of an anti-adherent.

4. The oral pharmaceutical tablet as defined in claim 1 wherein:
(a) the compressed immediate release core consists essentially of:
(i) 15-25% based upon the total weight of the compressed immediate release core of the pseudoephedrine sulfate or hydrochloride;
(ii) 75-85% based upon the total weight of the compressed immediate release core of a filler;
(iii) 0.1-1% based upon the total weight of the compressed immediate release core of a glidant;
(iv) 0.1-1% based upon the total weight of the compressed immediate release core of a lubricant;
(b) the delayed release coating (a)(2) on said compressed immediate release core consists essentially of:
(i) 25-45% based upon the total weight of the delayed release coating of a combination of at least two pH dependent polymers;
(ii) 3-10% based upon the total weight of the delayed release coating of a plasticizer;
(iii) 40-65% based upon the total weight of the delayed release coating of an anti-adherent;

(c) the pseudoephedrine immediate release coating comprises:
(i) 35-60% based upon the total weight of the pseudoephedrine immediate release coating of the pseudoephedrine sulfate or hydrochloride;
(ii) 20-35% based upon the total weight of the pseudoephedrine immediate release coating of a binder;
(iii) 1-10% based upon the total weight of the pseudoephedrine immediate release coating of a plasticizer;
(iv) 10-30% based upon the total weight of the pseudoephedrine immediate release coating of an anti-adherent;

(d) the antihistamine immediate release coating comprises:
(i) 5-15% based upon the total weight of the antihistamine immediate release coating of loratadine or descarboethoxy loratadine;
(ii) 40-60% based upon the total weight of the antihistamine immediate release coating of a binder;
(iii) 15-30% based upon the total weight of the antihistamine immediate release coating of a surfactant;
(iv) 5-15% based upon the total weight of the antihistamine immediate release coating of an anti-adherent.

5. The oral pharmaceutical tablet as defined in claim 1, wherein the pH dependent polymers are a combination of zein and methacrylic acid copolymer.

6. The oral pharmaceutical tablet as defined in claim 1, wherein the oral pharmaceutical tablet exhibits a pseudoephedrine dissolution profile similar to the pseudoephedrine dissolution profile shown in FIG. 1 when the oral pharmaceutical tablet is tested in a USP type I apparatus at 100 rpms, in 0.1N HCl with 0.1% tween 80.

7. An oral pharmaceutical tablet consisting of:
(a) a delayed release pseudoephedrine sulfate or hydrochloride tablet and
(b) an immediate release coating applied to said delayed release tablet that allows for the immediate release of a therapeutic amount of pseudoephedrine sulfate or hydrochloride and a therapeutic amount of an antihistamine selected from the group consisting of loratadine and descarboethoxy loratadine wherein the delayed release pseudoephedrine tablet consists of:
(a) a compressed immediate release core consisting of:
(i) 10-30% based upon the total weight of the compressed immediate release core of pseudoephedrine sulfate or hydrochloride;
(ii) 65-90% based upon the total weight of the compressed immediate release core of a filler;
(iii) 0.1-2% based upon the total weight of the compressed immediate release core of a glidant; and
(iv) 0.1-2% based upon the total weight of the compressed immediate release core of a lubricant;
(b) a delayed release coating on said compressed immediate release core consisting of:
(i) 15-60% based upon the total weight of the delayed release coating of a combination of at least two pH dependent polymers selected from the group consisting of zein, methacrylic acid copolymers, cellulose acetate phthalate, hydroxypropyl methylcellulose phthalate, hydroxypropyl methylcellulose acetate succinate, cellulose acetate trimellitate and polyvinyl acetate phthalate;

(ii) 3-15% based upon the total weight of the delayed release coating of a plasticizer; and
(iii) 30-75% based upon the total weight of the delayed release coating of an anti-adherent wherein the delayed release coating delays the release of the pseudoephedrine sulfate or hydrochloride from the compressed immediate release core until the delayed release tablet reaches an environment where the pH is higher than 6; and wherein the at least one immediate release coating consists of:
(a) a pseudoephedrine immediate release coating consisting of:
  (i) 20-70% based upon the total weight of the pseudoephedrine immediate release coating of pseudoephedrine sulfate or hydrochloride;
  (ii) 10-50% based upon the total weight of the pseudoephedrine immediate release coating of a binder;
  (iii) 1-15% based upon the total weight of the pseudoephedrine immediate release coating of a plasticizer;
  (iv) 10-40% based upon the total weight of the pseudoephedrine immediate release coating of an anti-adherent; and
(b) a separate antihistamine immediate release coating consisting of:
  (i) 1-25% based upon the total weight of the antihistamine immediate release coating of loratadine or descarboethoxy loratadine;
  (ii) 30-70% based upon the total weight of the antihistamine immediate release coating of a binder;
  (iii) 10-40% based upon the total weight of the antihistamine immediate release coating of a surfactant;
  (iv) 5-25% based upon the total weight of the antihistamine immediate release coating of an anti-adherent; and
(c) optionally a seal coat between the pseudoephedrine immediate release coating and the antihistamine immediate release coating.

8. The oral pharmaceutical tablet as defined in claim 7 wherein:
(a) the compressed immediate release core consists of:
  (i) 15-25% based upon the total weight of the compressed immediate release core of the pseudoephedrine sulfate or hydrochloride;
  (ii) 75-85% based upon the total weight of the compressed immediate release core of a filler;
  (iii) 0.1-1% based upon the total weight of the compressed immediate release core of a glidant;
  (iv) 0.1-1% based upon the total weight of the compressed immediate release core of a lubricant;
(b) the delayed release coating on said compressed immediate release core consists of:
  (i) 25-45% based upon the total weight of the delayed release coating of a combination of at least two pH dependent polymers;
  (ii) 3-10% based upon the total weight of the delayed release coating of a plasticizer;
  (iii) 40-65% based upon the total weight of the delayed release coating of an anti-adherent;
(c) the pseudoephedrine immediate release coating consists of:
  (i) 35-60% based upon the total weight of the pseudoephedrine immediate release coating of the pseudoephedrine sulfate or hydrochloride;
  (ii) 20-35% based upon the total weight of the pseudoephedrine immediate release coating of a binder;
  (iii) 1-10% based upon the total weight of the pseudoephedrine immediate release coating of a plasticizer;
  (iv) 10-30% based upon the total weight of the pseudoephedrine immediate release coating of an anti-adherent;
(d) the antihistamine immediate release coating consists of:
  (i) 5-15% based upon the total weight of the antihistamine immediate release coating of loratadine or descarboethoxy loratadine;
  (ii) 40-60% based upon the total weight of the antihistamine immediate release coating of a binder;
  (iii) 15-30% based upon the total weight of the antihistamine immediate release coating of a surfactant;
  (iv) 5-15% based upon the total weight of the antihistamine immediate release coating of an anti-adherent.

9. The oral pharmaceutical tablet as defined in claim 7, wherein the pH dependent polymers are a combination of zein and methacrylic acid copolymer.

10. An oral pharmaceutical tablet consisting of:
(a) a delayed release tablet consisting of:
  (i) a compressed immediate release core consisting of:
    (A) 15-25% based upon the total weight of the compressed immediate release core of a pseudoephedrine sulfate or hydrochloride;
    (B) 75-85% based upon the total weight of the compressed immediate release core of a filler;
    (C) 0.1-1% based upon the total weight of the compressed immediate release core of a glidant;
    (D) 0.1-1% based upon the total weight of the compressed immediate release core of a lubricant;
  (ii) a delayed release coating applied to the compressed immediate release core
  (a)(1) consisting of:
    (A) 25-45% based upon the total weight of the delayed release coating of a combination of zein and methacrylic acid copolymer and wherein the zein consists of 10-40% of the total weight of the delayed release coating;
    (B) 3-10% based upon the total weight of the delayed release coating of a plasticizer;
    (C) 40-65% based upon the total weight of the delayed release coating of an anti-adherent;
  wherein the delayed release coating delays the release of the pseudoephedrine from the compressed immediate release core until the delayed release tablet reaches an environment where the pH is higher than 6;
(b) a pseudoephedrine immediate release coating applied to the delayed release tablet consisting of:
  (i) 35-60% based upon the total weight of the pseudoephedrine immediate release coating of pseudoephedrine sulfate or hydrochloride;
  (ii) 20-35% based upon the total weight of the pseudoephedrine immediate release coating of a binder;
  (iii) 1-10% based upon the total weight of the pseudoephedrine immediate release coating of a plasticizer;
  (iv) 10-30% based upon the total weight of the pseudoephedrine immediate release coating of an anti-adherent;
(c) an antihistamine immediate release coating applied to the delayed release tablet consisting of:
  (i) 5-15% based upon the total weight of the antihistamine immediate release coating of loratadine or descarboethoxy loratadine;

(ii) 40-60% based upon the total weight of the antihistamine immediate release coating of a binder;
(iii) 15-30% based upon the total weight of the antihistamine immediate release coating of a surfactant;
(iv) 5-15% based upon the total weight of the antihistamine immediate release coating of an anti-adherent; and (d) optionally a seal coat between the pseudoephedrine immediate release coating and the antihistamine immediate release coating.

* * * * *